United States Patent
Bergström et al.

(10) Patent No.: US 6,283,755 B1
(45) Date of Patent: Sep. 4, 2001

(54) DENTAL IMPLANT COMPONENT

(75) Inventors: Nils Gustaf Bergström, Vagnhärad; Leif Broberg, Mölndal, both of (SE); Hansruedi Carisch, La Chaux-de-Fonds (CH); Anders Holmén, Hovås (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/355,714

(22) PCT Filed: Jul. 21, 1999

(86) PCT No.: PCT/SE99/01300

§ 371 Date: Aug. 3, 1999

§ 102(e) Date: Aug. 3, 1999

(87) PCT Pub. No.: WO00/04842

PCT Pub. Date: Feb. 3, 2000

(30) Foreign Application Priority Data

Jul. 23, 1998 (SE) .................................................. 9802605

(51) Int. Cl.$^7$ .................................................. A61C 13/10
(52) U.S. Cl. ......................................... 433/193; 433/201.1
(58) Field of Search ..................................... 433/175, 191, 433/192, 193, 201.1, 202.1

(56) References Cited

U.S. PATENT DOCUMENTS

| | | |
|---|---|---|
| 709,410 * | 9/1902 | Kelly ........................................ 433/172 |
| 3,716,418 | 2/1973 | Kochavi . |
| 4,431,420 * | 2/1984 | Adair ................................. 433/201.1 |
| 4,575,340 | 3/1986 | Lustig . |
| 4,684,555 * | 8/1987 | Neumeyer ........................... 433/201.1 |
| 5,180,303 | 1/1993 | Hornburg et al. . |
| 5,213,502 * | 5/1993 | Daftary .................................. 433/172 |
| 5,234,339 | 8/1993 | Grigereit . |
| 5,346,396 * | 9/1994 | Hakamatsuka ..................... 433/202.1 |
| 5,439,380 | 8/1995 | Marlin . |
| 5,447,435 | 9/1995 | Brodbeck . |
| 5,527,183 | 6/1996 | O'Brien . |
| 5,533,898 | 7/1996 | Mena . |
| 5,549,475 | 8/1996 | Duerr et al. . |
| 5,662,473 | 9/1997 | Rassoli et al. . |
| 5,681,167 | 10/1997 | Lazarof . |
| 5,688,123 | 11/1997 | Meiers et al. . |
| 5,716,215 * | 2/1998 | Blacklock ............................. 433/172 |
| 5,897,320 * | 4/1999 | Gittleman ........................... 433/201.1 |

* cited by examiner

Primary Examiner—Todd E. Manahan
(74) Attorney, Agent, or Firm—White & Case LLP

(57) ABSTRACT

Dental implant component (1; 1') for a dental prosthesis or a core part of a dental prosthesis to be fabricated on comprising a base section (3; 3') having a proximal end (2; 2') for engagement with a support end of a support component and a distal end (7; 7'); and an elongate post section (5; 5') which projects distally from the distal end of the base section and has a transverse dimension which is substantially less than the transverse dimension of the base section. In a first aspect of the invention the dental implant component is made at least in part from a material which is adapted to burn-out during lost-wax casting whereby a dental prosthesis or core part of a dental prosthesis fabricated on the dental implant component by lost wax casting includes at most only a part of the dental implant component. In a second aspect of the invention the elongate post section is positioned offset on the distal end of the base section.

16 Claims, 4 Drawing Sheets

DENTAL IMPLANT COMPONENT

FIELD OF THE INVENTION

The present invention relates to a dental implant component for a dental prosthesis or core part of a dental prosthesis to be fabricated on.

BACKGROUND OF THE INVENTION

Such a dental implant component is commonly referred to as a "cylinder" in the art but this term is not used herein when specifically referring to the present invention as it implies a circular cross-section of constant diameter for the component which is not the case with the present invention.

A dental prosthesis is one of the components which make up a dental implant which is a structure which is anchored to the jaw bone (maxilla or mandible) of a patient to replace one or more lost natural teeth. A dental implant comprises a dental prosthesis support structure which is anchored to the jaw bone of a totally or partially edentulous patient to support the dental prosthesis. The dental prosthesis support structure is typically formed by (i) one or more anchoring members (fixtures) implanted in the bone tissue of the maxilla or mandible, the number of fixtures used depending on whether the dental implant is to be for a single-tooth replacement, in which case a single fixture is used, or for a multi-tooth replacement, in which case one or, more usually, a plurality of fixtures will be used, and (ii) a transmucosal member (abutment) for each fixture, each abutment being connected to the coronal end of the associated fixture to bridge the soft tissue layer (gingiva) overlying the fixture site. A structure which presents one or more artificial replacement teeth—the dental prosthesis—is then connected to the coronal end(s) of the abutment(s), e.g. a crown for a single-tooth replacement or a bridge for replacement of a number of lost natural teeth.

To ensure that the dental prosthesis fits in with the prevailing conditions in the patient's oral cavity, for instance natural teeth still left in the maxilla or mandible, the dental prosthesis is fabricated with reference to a full-scale model of the toothless jaw prepared in a manner known per se. Usually incorporated in the model are one or more analogue components, the number corresponding to the number of fixtures in the maxilla or mandible. The or each analogue component has an end which is an analogue of the coronal end(s) presented by the dental prosthesis support structure, e.g. by the abutment(s). The analogue component(s) is incorporated into the model so that the analogue end(s) accurately reproduces the position and orientation that the coronal end(s) of the dental prosthesis support structure has, or will have, in the jaw.

A cylinder having a proximal or apical end which complements the coronal end(s) of the dental prosthesis support structure is then seated on the analogue end of each analogue component. A dental prosthesis which fits in with the prevailing conditions in the patient's oral cavity is then fabricated using the cylinder(s) whereupon the dental prosthesis is transferred to the dental prosthesis support structure for anchorage to the maxilla or mandible.

The manner in which the dental prosthesis is fabricated using the cylinder(s) depends on whether the dental prosthesis is for a single-tooth replacement or for replacing a number of teeth and also on whether the dental prosthesis is to be a permanent prosthesis or a temporary prosthesis for use in the interim period while a permanent prosthesis is fabricated.

Permanent dental prostheses are typically formed by applying a wax pattern on the cylinder(s) when mounted on the analogue component(s) and forming a cast structure on the cylinder(s) having the same profile as the wax pattern by the lost-wax casting process in which the cylinder-wax pattern assembly is surrounded by investment material and then "lost" by heating to leave a mould into which a precious or semi-precious metal such as gold is poured via a sprue passing through the investment material. In this regard, the cylinder(s) can be totally or partially formed of a burn-out material, e.g. a plastic such as polystyrene or Delrin™ (Du Pont), in which case the burn-out material is also selectively replaced by the metal. The use of the investment material, however, ensures that surface features provided at the apical end(s) of the cylinder(s), for example faces of a male or female polygon, which enable the cylinder(s) to seat on the coronal end(s) of the dental prosthesis support structure are retained in the cast structure when presented by burn-out material.

For a permanent single-tooth dental prosthesis a porcelain layer is fired onto the inner cast framework which includes, or is based on, a single cylinder to give a natural tooth appearance to the dental prosthesis. The wax pattern may or may not be shaped to give the inner cast framework a tooth-like appearance for the porcelain to be fired onto. If not, the porcelain layer is built-up on the framework to give the dental prosthesis a tooth-like form.

Where a number of natural teeth are to be permanently replaced, the dental prosthesis will typically comprise an inner cast framework which includes, or is based on, a number of cylinders and a range of artificial teeth (denture) mounted on the inner cast framework. In this instance, the wax pattern will typically splint the cylinders on the analogues in the model to form a cast framework which can bridge across the spaced-apart coronal ends of the dental prosthesis support structure and the denture will be mounted on the casting either before or after the casting is mounted on the coronal ends of the dental prosthesis support structure. Alternately, the dental prosthesis may be formed by applying an isolated wax pattern to each cylinder to form individual castings which are then mounted to the coronal ends of the dental prosthesis support structure with the denture then being mounted onto the castings.

For an overview on the formation of permanent dental prostheses see inter alia *'Dental Implants: A Guide for the General Practitioner'*, Michael Norton, Quintessence Publishing, 1995, Chapters 4 and 5.

The use of temporary dental prostheses is well-known and the circumstances in which a temporary dental prosthesis is needed are documented in U.S. Pat. No. 5,259,759 (Jorneus et al/Nobelpharma AB). In the case of a temporary single-tooth dental prosthesis, the usual procedure is to form an acrylic resin artificial tooth on the cylinder by applying the acrylic resin to the outer surface of the cylinder when mounted on the analogue end of the analogue in the model, shaping the acrylic resin to a natural tooth form and then curing the acrylic resin.

Although it is common for a dental prosthesis or core part of a dental prosthesis fabricated on one or more cylinders to be mounted to a fixture-abutment assembly or series of such assemblies, it is also known for a dental prosthesis or core part of a dental prosthesis fabricated on one or more cylinders to be mounted to a fixture or series of fixtures direct. In this case, the or each cylinder has a proximal end which complements the coronal end of the or each fixture and each analogue component in the model will have an end which is an analogue of the coronal end of the fixture(s).

The aim of the present invention is to provide a dental implant component for a dental prosthesis or core part of a dental prosthesis to be fabricated on which has advantages over the hitherto proposed cylinders in the art.

SUMMARY OF THE INVENTION

According to a first aspect of the present invention there is provided a dental implant component for a dental prosthesis or a core part of a dental prosthesis to be fabricated on by lost-wax casting comprising a base section having a proximal end for engagement with a support end of a support component and a distal end and an elongate post section which projects distally from the distal end of the base section and has a transverse dimension which is substantially less than the transverse dimension of the base section, at least a part of the dental implant component being made from a material adapted to burn-out during lost-wax casting. The dental prosthesis or core part formed will thus include none or some of the dental implant component depending on the degree to which the component is made from the burn-out material. Where the dental implant component is partially formed of a material adapted to burn-out during lost-wax casting, the part of the dental implant component included in the dental prosthesis or core part may be that part of the dental implant component which presents the proximal end thereof.

According to a second aspect of the present invention there is provided a dental implant component for a dental prosthesis or core part of a dental prosthesis to be fabricated on comprising a base section having a proximal end for engaging a support end of a support component and a distal end and an elongate post section which projects distally from the distal end of the base section, the elongate post section having a transverse dimension substantially less than the transverse dimension of the base section and being positioned offset on the distal end of the base section.

A dental implant component according to the invention has an increased outer surface area by virtue of the post section having a transverse dimension which is substantially less than the transverse dimension of the base section with the consequence that a wax pattern applied to the dental implant component will cool at a faster rate thereby enabling the fabrication process for a dental prosthesis to be speeded up. The fact that the post section has a transverse dimension which is substantially less than the transverse dimension of the base section also enables a portion of the distal end of the base section to act as a support surface for the dental prosthesis or core part formed thereon thus improving the stability of the dental prosthesis. Moreover, the length of the post section can be selected such that a distal section thereof will project from a core- or dental prosthesis-forming wax pattern or acrylic resin artificial tooth applied to the dental implant component for a technician to pick-up the assembly.

The support component may be a member of a dental prosthesis support structure which presents the coronal end of the dental prosthesis support structure, for example a fixture or abutment sleeve or an analogue of the member of the dental prosthesis support structure embedded in a model.

In an embodiment of the invention such as those hereinafter to be described the transverse dimension of the post section at the distal end of the base section is no more than approximately half the transverse dimension of the distal end of the base section.

In an embodiment of the invention according to its first aspect such as those hereinafter to be described the post section is positioned offset on the distal end of the base section. The post section of the dental implant component according to the first aspect may, however, be positioned centrally on the distal end of the base section instead.

In an embodiment of the invention such as one hereinafter to be described the base section is hollow having an internal cavity with an open end in the proximal end and the post section is solid.

In an alternative embodiment of the invention such as one hereinafter to be described the dental implant component is in the form of a sleeve having an open-ended channel which extends through the base and post sections. This construction has particular advantages when a core part of a dental prosthesis is fabricated on the dental implant component by lost-wax casting and the dental prosthesis is to be cemented to a dental prosthesis support structure anchored to the jaw bone because the open-ended channel in the dental implant component facilitates the formation of a vent channel in the dental prosthesis for relieving the hydrostatic pressures associated with the cementation. These advantages may also be realised if the dental implant component is hollow having an internal cavity which extends distally from an open end in the proximal end through the base section and into the post section, as in an embodiment of the invention hereinafter to be described.

A dental implant component in accordance with the second aspect of the invention has particular, but not exclusive, application for fabrication of a dental prosthesis or a core part of a dental prosthesis by lost-wax casting. With this in mind, the dental implant component may be formed wholly from a material adapted to remain intact or burn-out during lost-wax casting or partially from a material adapted to burn-out during lost-wax casting. The dental prosthesis or core part formed will thus include all, none or some of the dental implant component respectively.

Exemplary embodiments of the invention will now be described with reference to the accompanying Figures of drawings.

DETAILED DESCRIPTION OF THE EXEMPLARY EMBODIMENTS OF THE INVENTION

Figure 1:
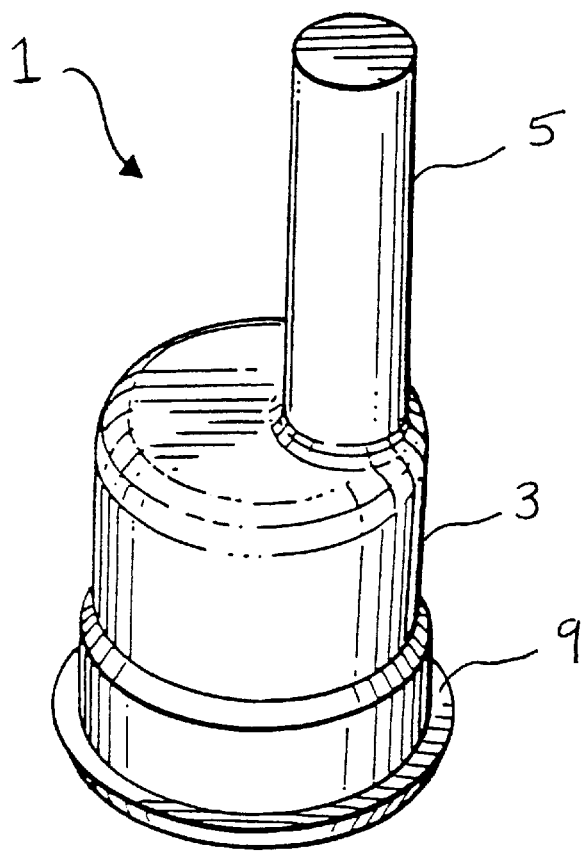
FIG. 1 is a perspective view from above of a dental implant component according to a first embodiment of the invention.
Figure 2:
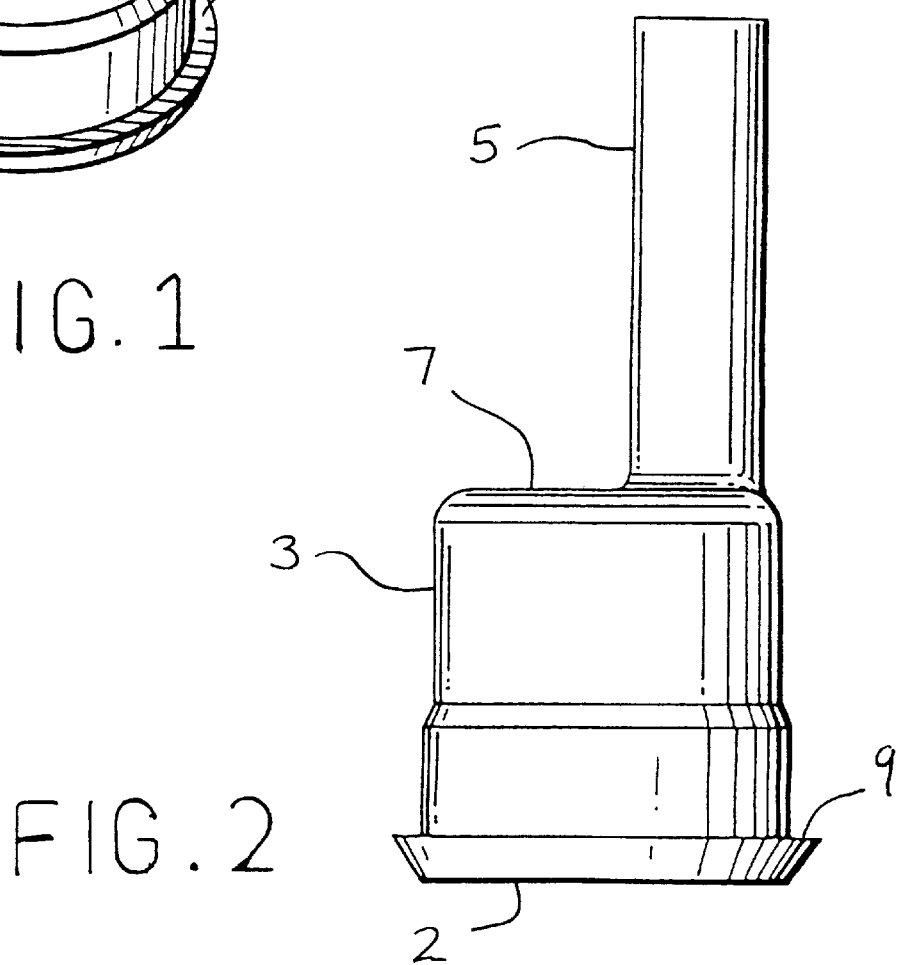
FIG. 2 is a side view of the dental implant component of FIG. 1.
Figure 3:
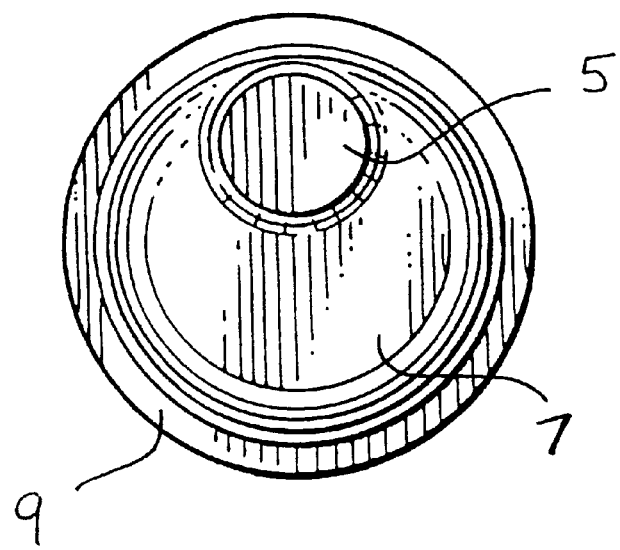
FIG. 3 is a plan view of the dental implant component of FIG. 1.
Figure 4:
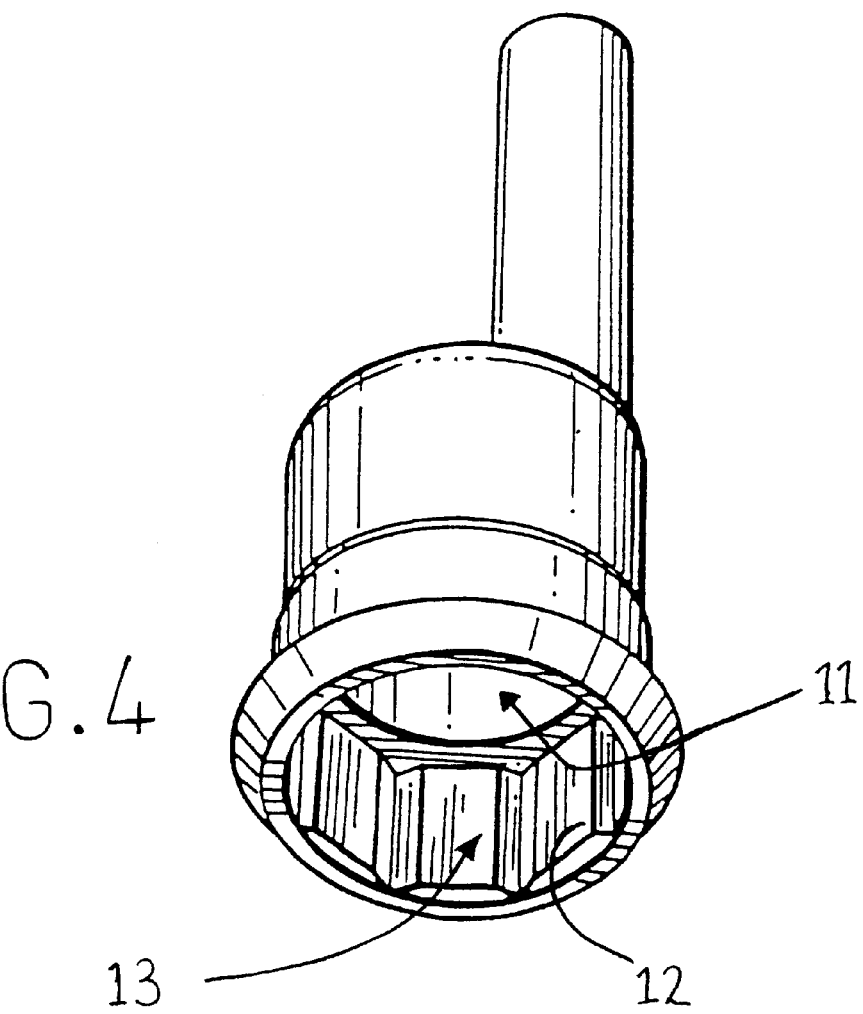
FIG. 4 is a perspective view from below of the dental implant component of FIG. 1.
Figure 5:
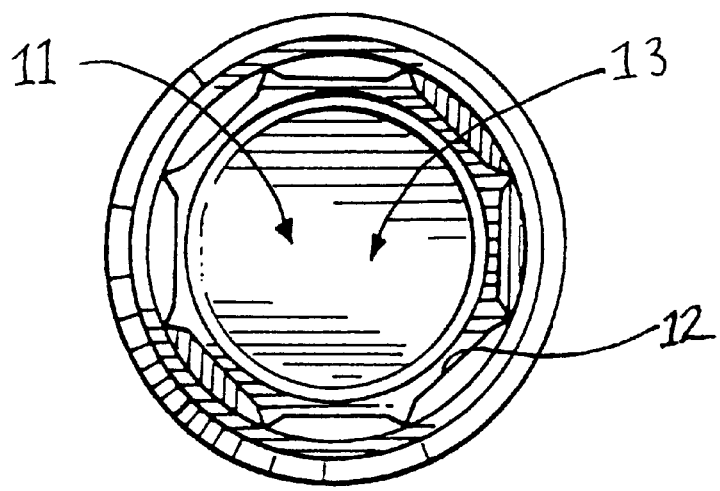
FIG. 5 is an underneath view of the dental implant component of FIG. 1.
Figure 6:
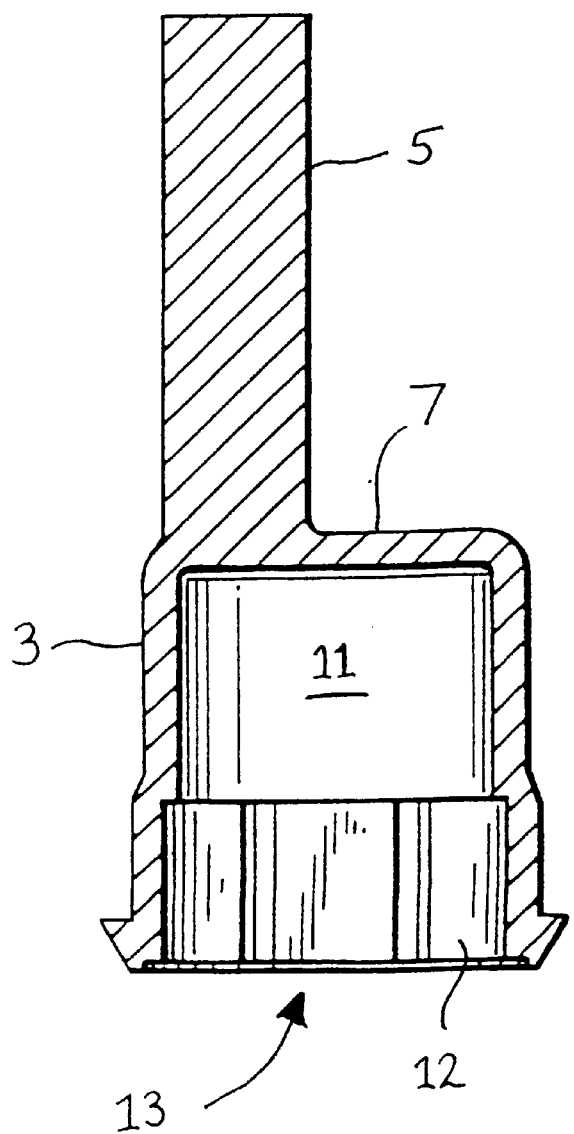
FIG. 6 is a cross-sectional side view of the dental implant component of FIG. 1.

In FIGS. 1 to 6 there is shown a dental implant component 1 according to a first embodiment of the present invention which, in this particular example, is to be used in the fabrication of a core part of a single-tooth dental prosthesis by lost-wax casting.

With this in mind, the dental implant component 1 is made from a plastic material which will burn-out during lost-wax casting. The dental implant component 1 could, however, also be formed only partially from a burn-out material or wholly from a non-burn-out material, e.g. a high melting point metal.

The dental implant component 1 has a base 3 having a proximal end 2 and a distal end presented by a roof 7. The base 3 is hollow having a cavity 11 which extends from a opening 13 in the proximal end 2 to the inner surface of the roof 7. The opening 13 of the cavity 11 has an octagonal cross-section 12 for anti-rotational coupling and indexing with a complementary octagonal cross-section on the end of an analogue structure in a model of a jaw of a partially edentulous patient, which end is an analogue of the coronal end of an abutment sleeve (not shown) secured, or to be secured, to a fixture (not shown) which is implanted in the bone tissue of the jaw of the patient and to which the single-tooth dental prosthesis is to be secured.

The abutment sleeve is a part of a two-piece abutment and has an axial, open-ended channel therethrough. The second part of the abutment is an abutment screw which is adapted to pass through the channel in the abutment sleeve and screw into an internally-threaded socket in the fixture for screw retention of the abutment sleeve to the fixture.

The dental implant component 1 further comprises a narrow elongate solid post or chimney 5 positioned offset on the roof 7 of the base 3. The length of the post 5 is such that it will project from a wax pattern built-up on the dental implant component 1. For support of the wax pattern the bottom of the base 3 is provided with an annular ledge 9. Further support for the wax pattern can be provided by the roof 7.

In use of the dental implant component 1 in the fabrication of a core part of a single-tooth dental prosthesis by lost-wax casting, the dental implant component 1 is firstly mounted on the analogue end of the analogue structure (the "abutment analogue") in the model. A wax pattern is then built-up on the dental implant component 1 around the post 5 such that the post 5 projects distally from the wax pattern.

The dental implant component-wax pattern assembly is then picked-up off the abutment analogue and transferred to a lost-wax casting apparatus through use of the distal section of the post 5 which projects through the wax pattern. The projecting distal section of the post 5 is then removed and investment material packed into the cavity 11 of the base 3 and around the outer surfaces of the wax pattern to form a mould. A molten precious metal such as gold is then poured into the mould via a sprue extending through the investment material after the wax and plastic material of the dental implant component 1 have been burnt off. After cooling, a metal casting is formed having the outer surface profile of the wax pattern and the inner surface profile, including the octagonal cross-section 12, of the cavity 11 in the base 3.

A porcelain layer is then fired to the casting to give a single-tooth prosthesis with a natural tooth finish and shape after which the single-tooth prosthesis is cemented to the abutment sleeve with the complementary octagonal cross-sections of the dental prosthesis and abutment sleeve ensuring that the prosthesis has the correct orientation in the oral cavity and is secured against rotation on the fixture-abutment assembly.

The dental implant component 1 has the advantage of providing (i) means for dismounting the dental implant component 1 from the abutment analogue after the wax pattern has been applied, (ii) an increased outer surface area by virtue of the step formed between the base 3 and the post 5 thereby enabling the rate at which the wax is cooled down to be speeded up, and (iii) a supplementary support surface for the wax pattern and cast core part in the form of the step between the base 3 and the post 5, that is to say, the roof 7.

To alleviate the hydrostatic pressures generated on cementing a single-tooth dental prosthesis formed through lost-wax casting as above to the dental prosthesis support structure in the jaw bone it is generally necessary to provide a vent in the prosthesis. This typically requires forming a vent channel in the occlusal surface of the prosthesis by firing the porcelain around an access pin to form an access passage in the porcelain and then drilling through the occlusal surface of the cast core part via the access passage in the porcelain layer. After cementing of the prosthesis the vent channel is plugged with a suitable cosmetic material.

Figure 7:
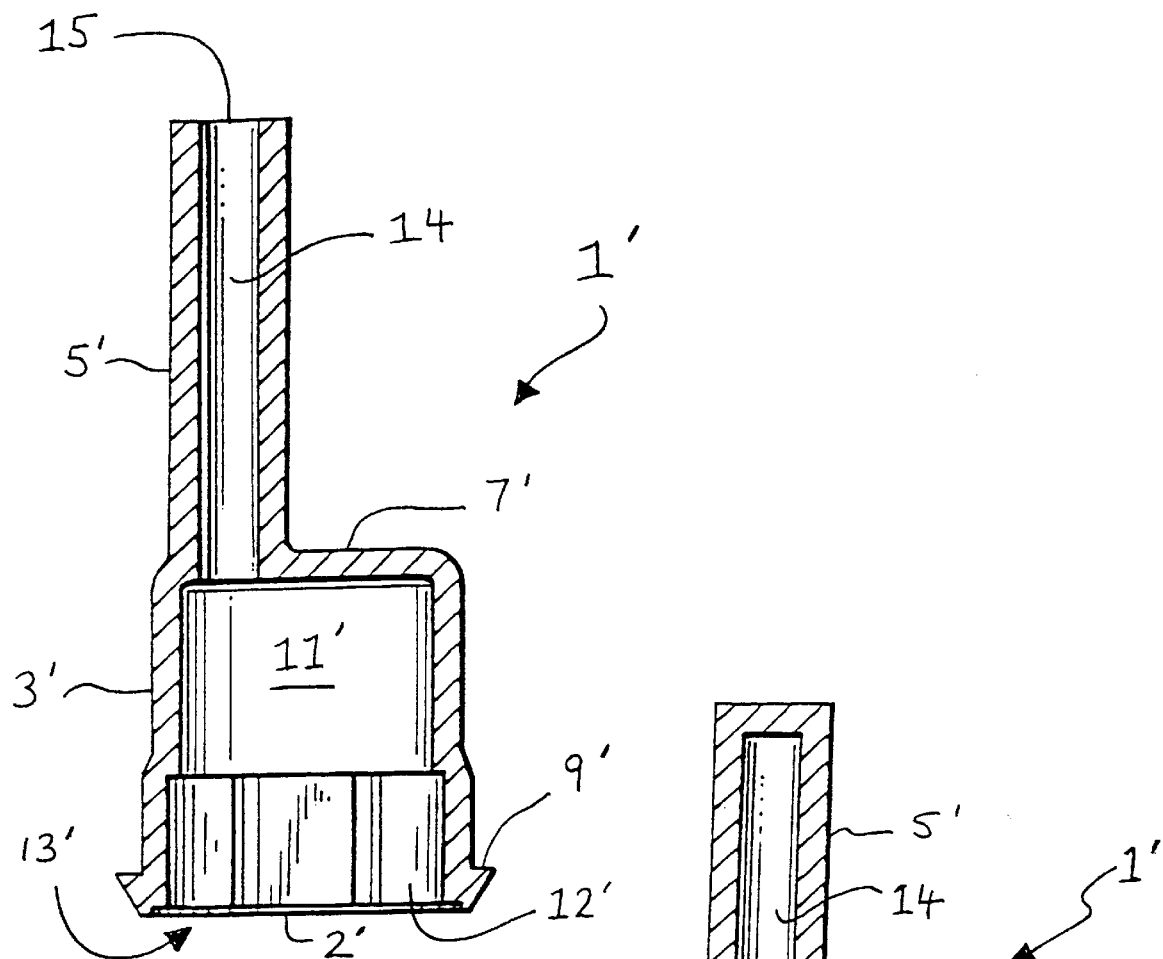
FIG. 7 is a cross-sectional side view of a dental implant component according to a second embodiment of the invention.

In FIG. 7 there is shown a dental implant component 1' according to a second embodiment of the present invention which is able to alleviate the aforementioned difficulty in drilling through the cast core part to provide a vent channel for relieving the hydrostatic pressures generated on cementing the single-tooth dental prosthesis to the dental prosthesis support structure.

The dental implant component 1' is a modification of the dental implant component 1 hereinabove described with reference to FIGS. 1 to 6 and for that reason like reference numbers are used in FIG. 7 to indicate like parts.

The difference between the dental implant component 1' of FIG. 7 and the dental implant component 1 of FIGS. 1 to 6 is that the post 5' of the dental implant component 5' is formed with a channel 14 therein which communicates with the cavity 11' such that the dental implant component 1' takes the form of a sleeve having a first open end 13' at the proximal end 2' of the base 3' and a second open end 15 at the free end of the post 5'. The result of the sleeve form of the dental implant component 1' is that the channel 14 and cavity 11' will be reproduced in a core part formed on the dental implant component 1' by lost-wax casting by virtue of investment material filling the channel 14 and cavity 11'. This then allows a rod of, for instance, graphite to be inserted into the channel 14 prior to the application of the tooth-like material to the cast core part, e.g. by firing of a porcelain layer onto the core part. Removal of the graphite rod will then leave a vent channel through the dental prosthesis. If it is not possible to simply pull out the graphite rod then the rod can be removed by drilling. Drilling of the graphite rod is far easier than through the metal casting as would be needed with the dental implant component 1 hereinabove described with reference to FIGS. 1 to 6.

The dental implant component 1' thus has the advantages of the dental implant component 1 of FIGS. 1 to 6 detailed above with the further advantage of simplifying the provision of a vent channel through a core part of a dental prosthesis fabricated thereon for relieving the hydrostatic pressures generated on cementing the dental prosthesis to the dental prosthesis support structure anchored to the jaw bone. A further advantage is that there is less likelihood of air pockets being formed in the investment material positioned in the dental implant component 1' than would be the case with the dental implant component 1 of FIGS. 1 to 6 since the investment material will extend through the dental implant component 1' rather than being blocked by an internal wall such as the roof 7 in the dental implant component 1 of FIGS. 1 to 6.

Figure 8:
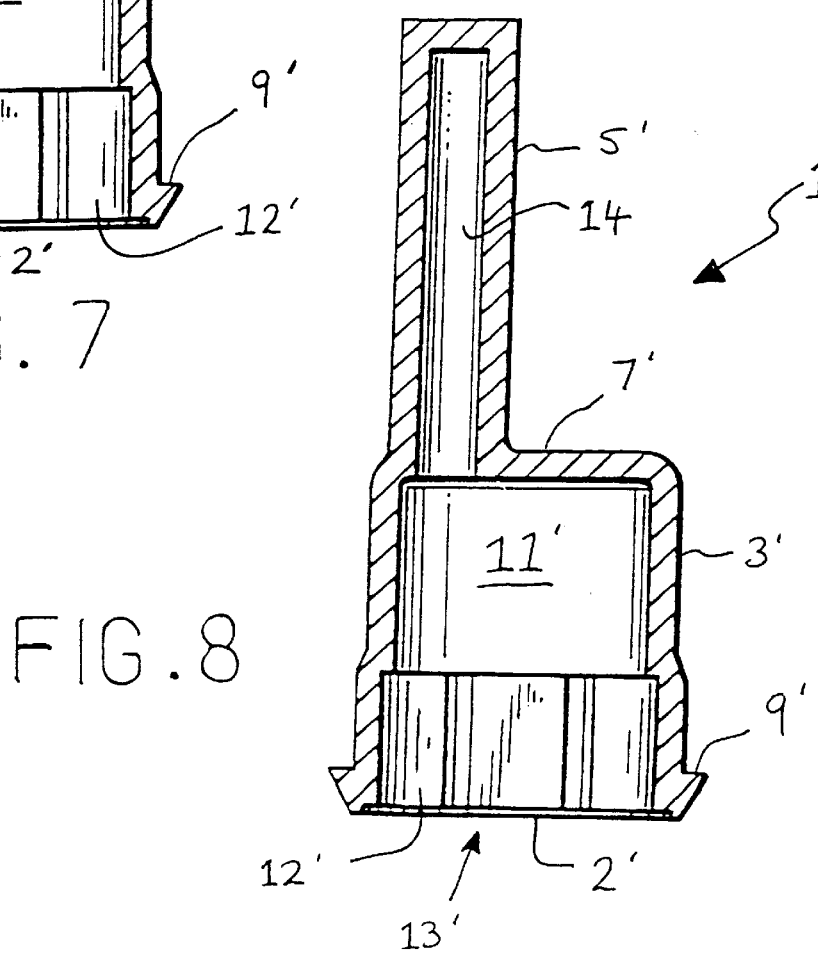
FIG. 8 is a cross-sectional side view of a modified version of the dental implant component of FIG. 7.

The vent channel in the dental prosthesis could also be formed if the channel 14 in the post 5' were closed off at the free end of the post 5' because removal of the distal section of the post 5' projecting from the wax pattern would expose an open-ended channel for investment material to be packed into for reproducing the open-ended channel in the cast core part. Such a modified version of the dental implant component 1' is shown in FIG. 8.

It will be understood that the present invention has been described with reference to exemplary embodiments and that the invention can be varied in many ways within the scope of the appended claims. For example, although the exemplary dental implant components of the present invention have been described with reference to the fabrication of a core part of a single-tooth dental prosthesis by lost-wax casting, dental implant components of the invention may also be used for forming a core part of a multi-tooth dental prosthesis, e.g. a bridge, in a similar manner and also for the formation of a temporary dental prosthesis, for example a temporary single-tooth dental prosthesis in which an acrylic resin artificial tooth is formed on the dental implant component. Moreover, individual features of the exemplary embodiments may have equal application in other embodiments of the invention either in isolation or in combination with other features of the exemplary embodiments.

Finally, the inclusion in the appended claims of reference numerals used in the accompanying Figures of drawings is for illustrative purposes and not to be construed as having a limiting effect on the scope of the claims.

What is claimed is:

1. A wax-receiving, fabrication-intermediate component of a dental prosthesis or a core part of a dental prosthesis, comprising:
    a base section having a proximal end comprising means for engagement with a support end of a support component of a dental implant system, a distal end being spaced in an axial direction from the proximal end and presenting a distal top cross-sectional area having a transverse dimension, and a lateral surface extending from the distal end towards the proximal end;
    an elongate post section having an outer post surface, an axial dimension and a transverse dimension, said elongate post section projecting in the axial direction distally from the distal end of the base section, wherein the transverse dimension of the post section is substantially less than said transverse dimension of the distal end of the base section, so that a step surface is thereby formed by the distal end of the base section; and
    an outer wax-receiving surface consisting of said lateral surface of the base section, said step surface of the distal end and a part of said post surface from a point where the post projects from the distal end to a more distal point along the axial dimension of the post section wherein the more distal point is proximal to the most distal point,
    wherein the wax-receiving component at least partly is made from a burnout material in order to form a mold cavity for the dental prosthesis or core part of the dental prosthesis in a lost-wax casting process.

2. A wax-receiving, fabrication-intermediate component of a dental prosthesis or a core part of a dental prosthesis, comprising:
    a base section having a proximal end comprising means for engagement with a support end of a support component of a dental implant system, a distal end being spaced in an axial direction from the proximal end and presenting a distal top cross-sectional area having a transverse dimension, and a lateral surface extending from the distal end towards the proximal end;
    an elongate post section having an outer post surface, an axial dimension, a transverse dimension and a cross-sectional area, said elongate post section projecting in the axial direction distally from the distal end of the base section, wherein the transverse dimension of the post section is substantially less than said transverse dimension of the distal end of the base section, so that a step surface is thereby formed by the distal end of the base section, wherein said step surface is larger than the cross-sectional area of the post section at the distal end; and
    an outer wax-receiving surface consisting of said lateral surface of the base section, said step surface of the distal end and a part of said post surface from a point where the post projects from the distal end to a more distal point along the axial dimension of the post section wherein the more distal point is proximal to the most distal point,
    wherein the wax-receiving component is made entirely from a non-burnout material in order to remain intact in a lost-wax casting process and form part of the dental prosthesis or core part of the dental prosthesis.

3. The component as claimed in claim 1 or 2, wherein the transverse dimension of the post section at the distal end of the base section is no more than approximately half the transverse dimension of the distal end of the base section.

4. The component as claimed in claim 1 or 2, wherein the post section is positioned offset on the distal end of the base section.

5. The component as claimed in claim 4, wherein the transverse dimension of the post section at the distal end of the base section is no more than approximately half the transverse dimension of the distal end of the base section.

6. The component as claimed in claim 1 or 2, wherein the component is hollow having an internal cavity which extends distally from an open end in the proximal end through the base section and into the post section.

7. The component as claimed in claim 1 or 2, wherein the component is in the form of a sleeve having an open-ended channel which extends through the base and post sections.

8. The component as claimed in claim 1 or 2, wherein the base section is hollow having an internal cavity with an open end in the proximal end and the post section is solid.

9. A mold cavity forming assembly for use in the fabrication of a dental prosthesis or a core part of a dental prosthesis by lost-wax casting, comprising:
    (i) a wax-receiving component, made at least partly from a burnout material and comprising:
        a base section having a proximal end comprising engagement means for engagement with a support end of a support component of a dental implant system, and a distal end presenting a presenting a distal top cross-sectional area having a transverse dimension, and
        an elongate post section projecting distally from the distal end of the base section, said post section having a transverse dimension which is substantially less than said transverse dimension of the distal end, thereby providing a step at the distal end of the base section, wherein the base section and the post section provide an outer surface area; and
    (ii) a wax pattern in the form of a tooth applied on at least a part of said outer surface area, wherein at least a part of the post section projects distally from the wax pattern.

10. A mold cavity forming assembly for use in the fabrication of a dental prosthesis or a core part of a dental prosthesis by lost-wax casting, comprising:

(i) a wax-receiving component, which is made entirely from a non-burnout material in order to remain intact in a lost-wax casting process and comprising:

a base section having a proximal end comprising engagement means for engagement with a support end of a support component of a dental implant system, and a distal end presenting a distal top cross-sectional area having a transverse dimension, and an elongate post section projecting distally from the distal end of the base section, said post section having a transverse dimension which is substantially less than said transverse dimension of the distal end, thereby providing a step at the distal end of the base section, wherein the base section and the post section provide an outer surface area; and (ii) a wax pattern in the form of a tooth applied on at least a part of said outer surface area, wherein at least a part of the post section projects distally from the wax pattern.

11. The assembly as claimed in claim 9 or 10, wherein the transverse dimension of the post section at the distal end of the base section is no more than approximately half the transverse dimension of the distal end of the base section.

12. The assembly as claimed in claim 9 or 10, wherein the post section is positioned offset on the distal end of the base section.

13. The assembly as claimed in claim 12, wherein the transverse dimension of the post section at the distal end of the base section is no more than approximately half the transverse dimension of the distal end of the base section.

14. The assembly as claimed in claim 9 or 10, wherein the base section is hollow having an internal cavity with an open end in the proximal end and the post section is solid.

15. The assembly as claimed in claim 9 or 10, wherein the wax-receiving component is hollow having an internal cavity which extends distally from an open end in the proximal end through the base section and into the post section.

16. The assembly as claimed in claim 9 or 10, wherein the wax-receiving component is in the form of a sleeve having an open-ended channel which extends through the base and post sections.

* * * * *